US010653829B2

(12) United States Patent
Barchen et al.

(10) Patent No.: US 10,653,829 B2
(45) Date of Patent: May 19, 2020

(54) AUTOMATIC INJECTOR HAVING DOOR BLOCK UNTIL PROPER CARTRIDGE INSERTION

(71) Applicant: West Pharma. Services IL, Ltd., Ra'anana (IL)

(72) Inventors: Lior Barchen, Gani Tal (IL); Yossi Bar-el, Beit Arye (IL)

(73) Assignee: WEST PHARMA. SERVICES IL, LTD., Ra'anana (IL)

(*) Notice: Subject to any disclaimer, the term of this patent is extended or adjusted under 35 U.S.C. 154(b) by 0 days.

(21) Appl. No.: 16/321,185

(22) PCT Filed: Dec. 21, 2016

(86) PCT No.: PCT/US2016/068058
§ 371 (c)(1),
(2) Date: Jan. 28, 2019

(87) PCT Pub. No.: WO2018/026386
PCT Pub. Date: Feb. 8, 2018

(65) Prior Publication Data
US 2019/0167894 A1 Jun. 6, 2019

Related U.S. Application Data

(60) Provisional application No. 62/369,513, filed on Aug. 1, 2016.

(51) Int. Cl.
*A61M 5/14* (2006.01)
*A61M 5/142* (2006.01)
*A61M 5/145* (2006.01)

(52) U.S. Cl.
CPC ...... *A61M 5/14248* (2013.01); *A61M 5/1456* (2013.01); *A61M 5/1452* (2013.01);
(Continued)

(58) Field of Classification Search
CPC ............ A61M 5/14248; A61M 5/1456; A61M 2005/14268; A61M 2005/14573
See application file for complete search history.

(56) References Cited

U.S. PATENT DOCUMENTS 4,689,043 A  8/1987  Bisha
5,090,877 A  2/1992  D'Silva
(Continued)

FOREIGN PATENT DOCUMENTS

WO    2012032411 A2       3/2012
WO    WO-2012032411 A2 *  3/2012  ........ A61M 5/14244

OTHER PUBLICATIONS

Int'l Search Report dated Apr. 20, 2017 in Int'l Application No. PCT/US2016/068058.
(Continued)

*Primary Examiner* — Nathan R Price
*Assistant Examiner* — Courtney B Fredrickson
(74) *Attorney, Agent, or Firm* — Panitch Schwarze Belisario & Nadel LLP

(57) ABSTRACT

An automatic injector device for delivering a pharmaceutical substance from a cartridge having a protruding edge, positioned in a housing cartridge bay having an opening sized to allow passage of the cartridge; a door to the cartridge bay opening, the door connected to the housing and having an unlatched position and a latched position, the door defining a trajectory between the unlatched position and the latched position; an interference element having a deflected and an inflected orientation, the deflected orientation mechanically interferes with the trajectory of the door; and a contact interface positioned along the cartridge bay and extending up to the protruding edge, the contact interface mechanically couples the deflected and inflected orientation with a sensed contact of the protruding edge, such that when the protruding edge is positioned at the contact interface, the contact
(Continued)

interface shifts the interference element into the inflected orientation.

18 Claims, 12 Drawing Sheets

(52) U.S. Cl.
CPC ............ *A61M 2005/14268* (2013.01); *A61M 2005/14573* (2013.01)

(56) References Cited

U.S. PATENT DOCUMENTS

| | | |
|---|---|---|
| 5,364,364 A | 11/1994 | Kasvikis et al. |
| 5,445,621 A | 8/1995 | Poli et al. |
| 5,505,709 A | 4/1996 | Funderburk et al. |
| 5,779,676 A | 7/1998 | Kriesel et al. |
| 5,830,187 A | 11/1998 | Kriesel et al. |
| 5,954,697 A | 9/1999 | Srisathapat et al. |
| 6,423,036 B1 | 7/2002 | Van Huizen |
| 6,599,272 B1 | 7/2003 | Hjertman et al. |
| 9,421,323 B2 | 8/2016 | Cabiri et al. |
| 2007/0197968 A1 | 8/2007 | Pongpairochana et al. |
| 2011/0066131 A1 | 3/2011 | Cabiri |
| 2014/0188073 A1* | 7/2014 | Cabiri ............... A61M 5/14244 604/506 |

OTHER PUBLICATIONS

Int'l Preliminary Report on Patentability dated Feb. 5, 2019 in Int'l Application No. PCT/US2016/068058.

* cited by examiner

FIG. 1 — Flow chart of inserting cartridge and closing door
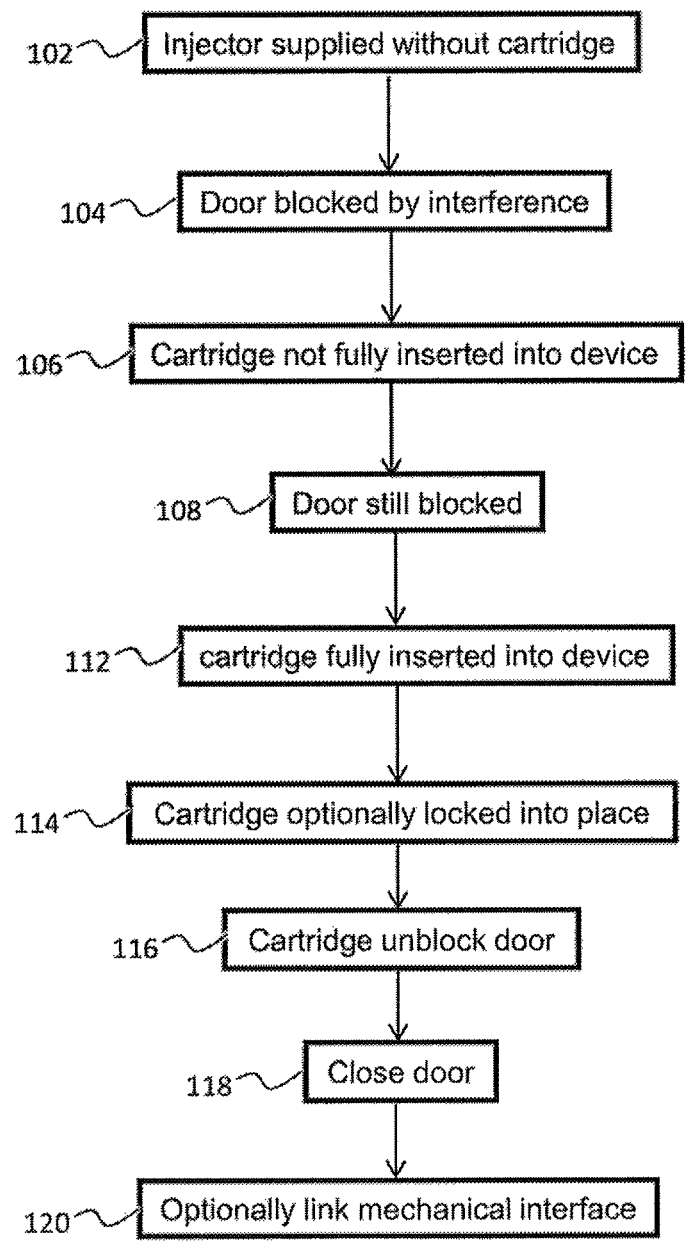

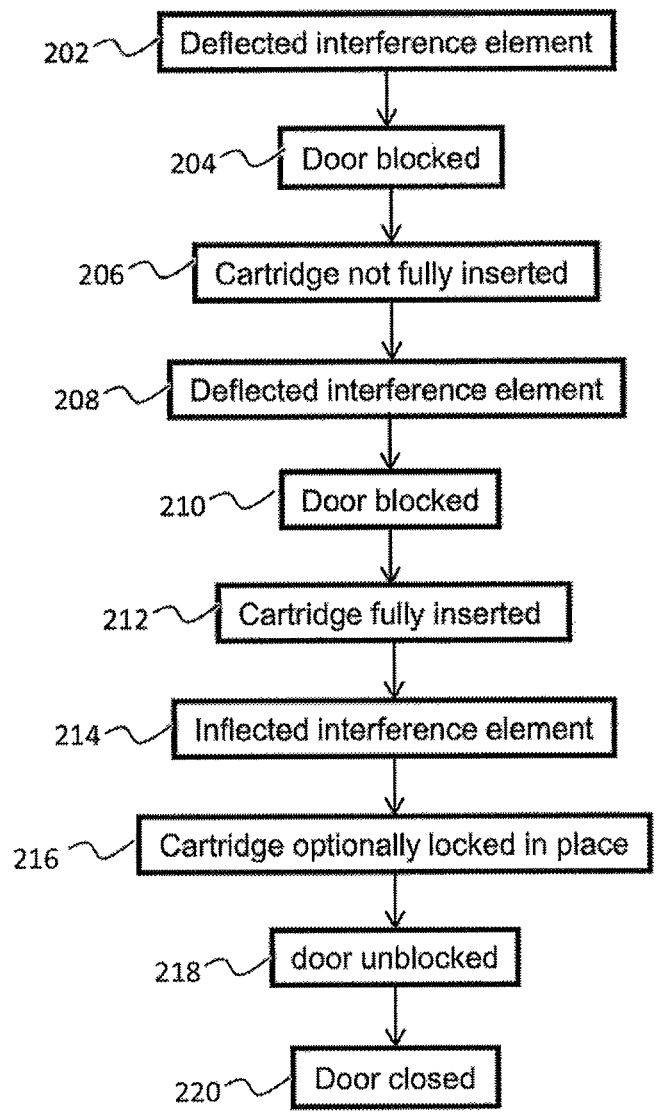
FIG. 2 – State diagram of inserting cartridge and closing door

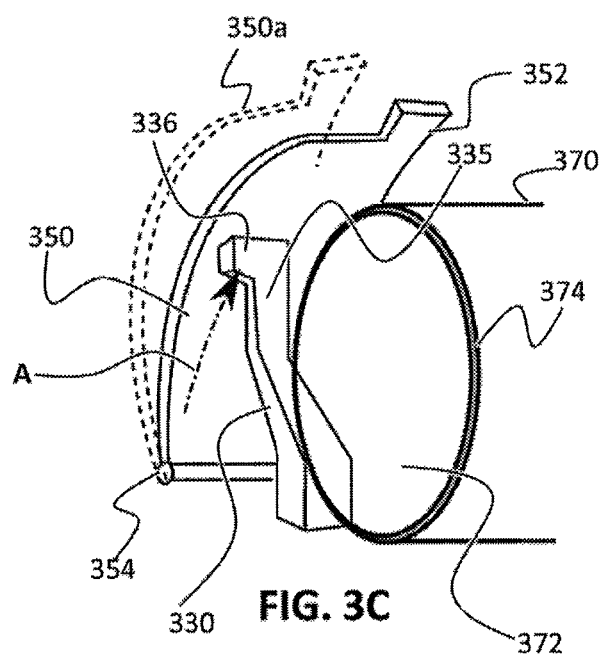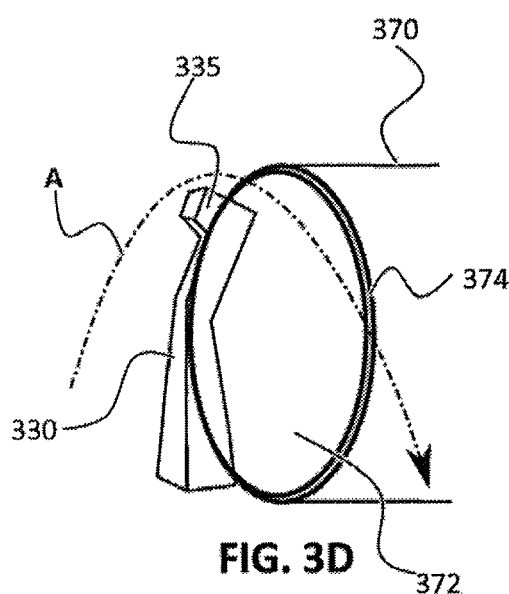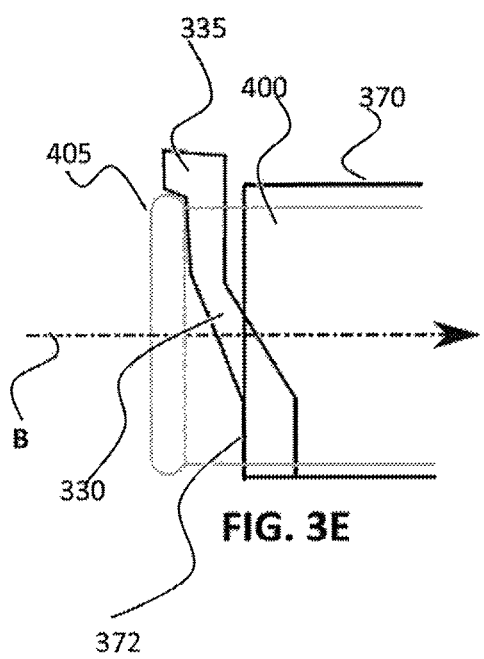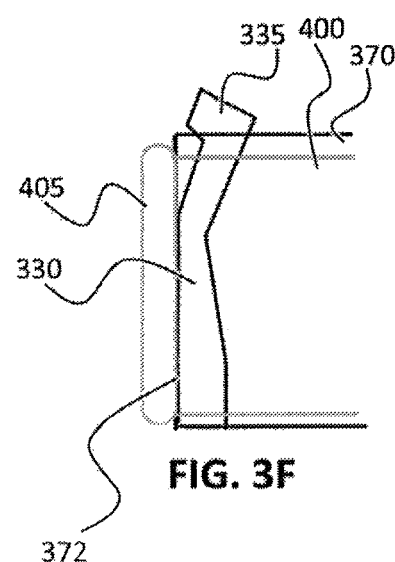

FIG. 4A – Drawing of elements door stop mechanism
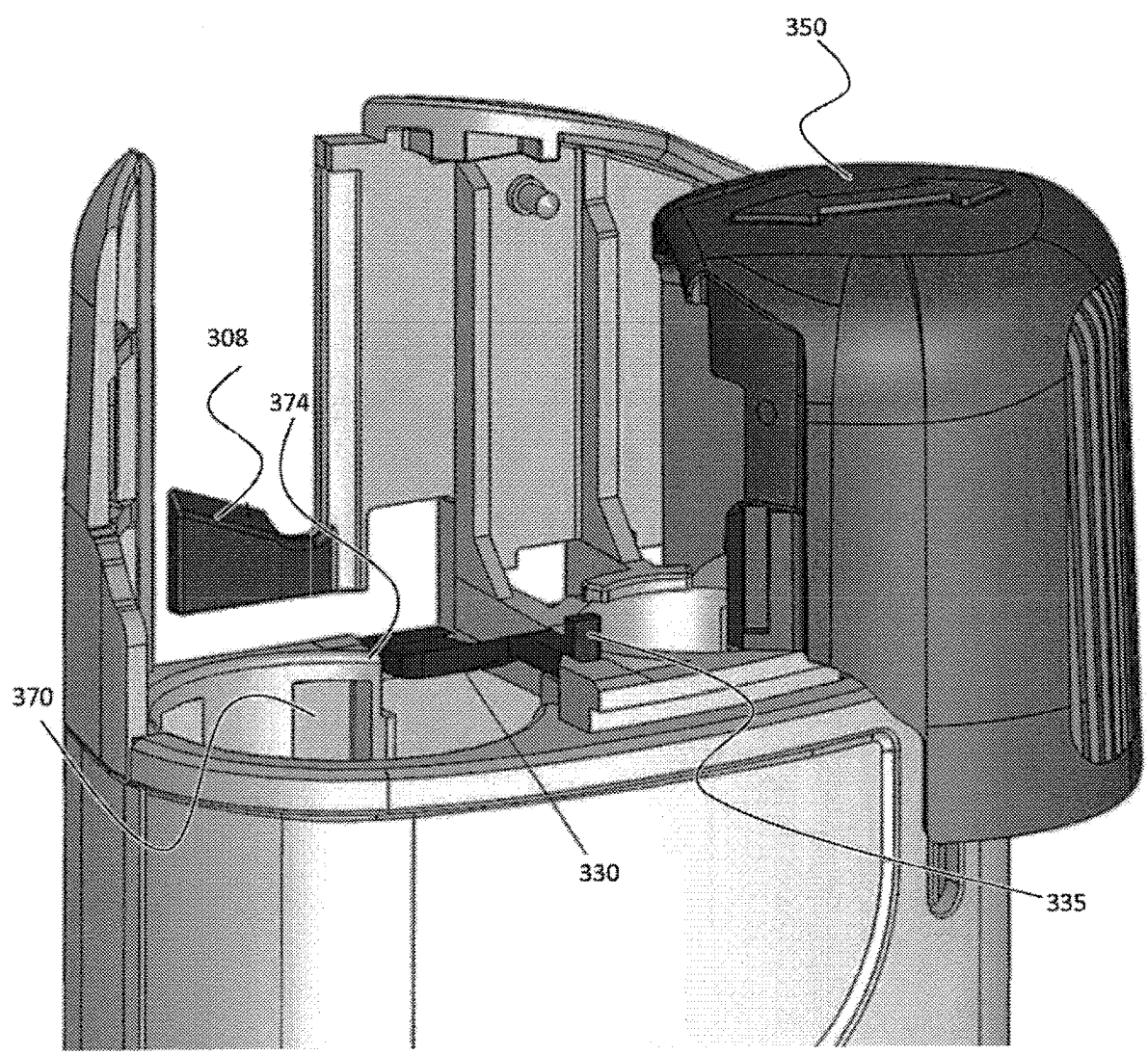

FIG. 4B – Drawing of SD 3.5 with door stop mechanism
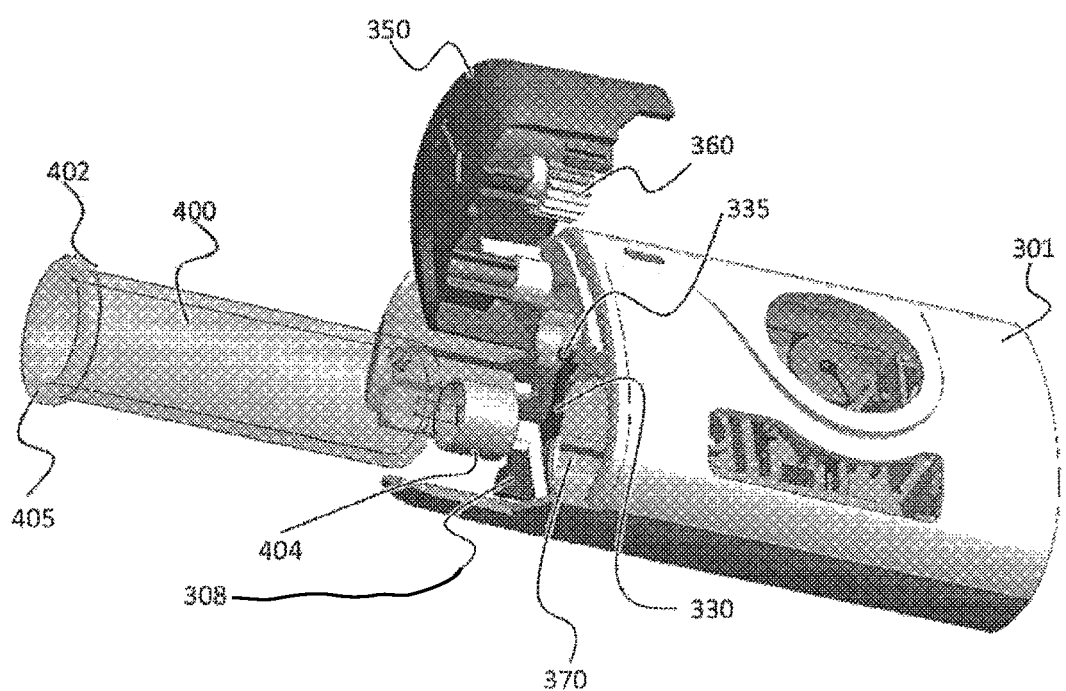

FIG. 5 – Cartridge inserted door closed
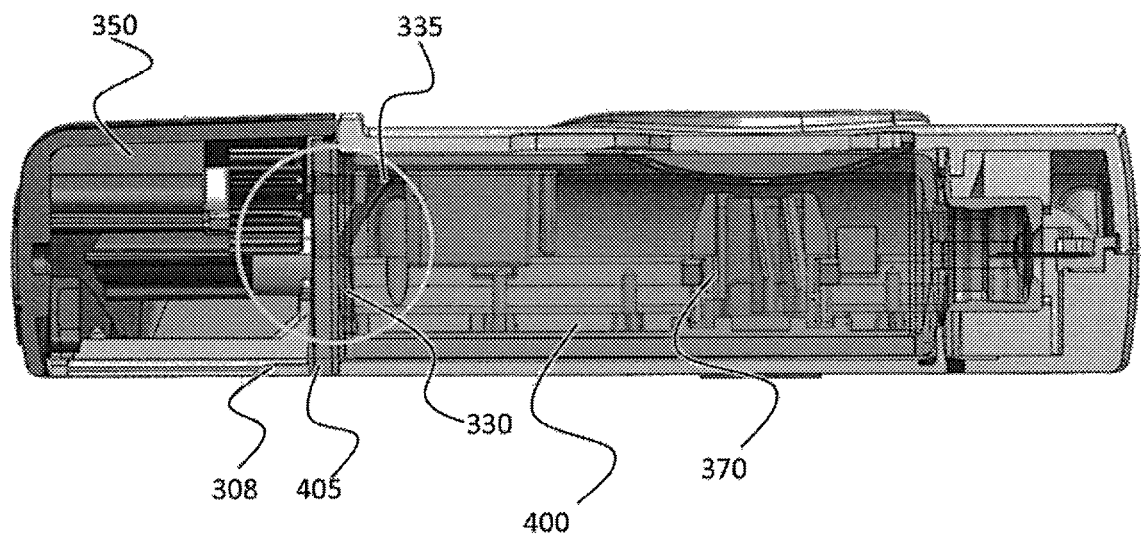

FIG. 6A – No Cartridge inserted door blocked
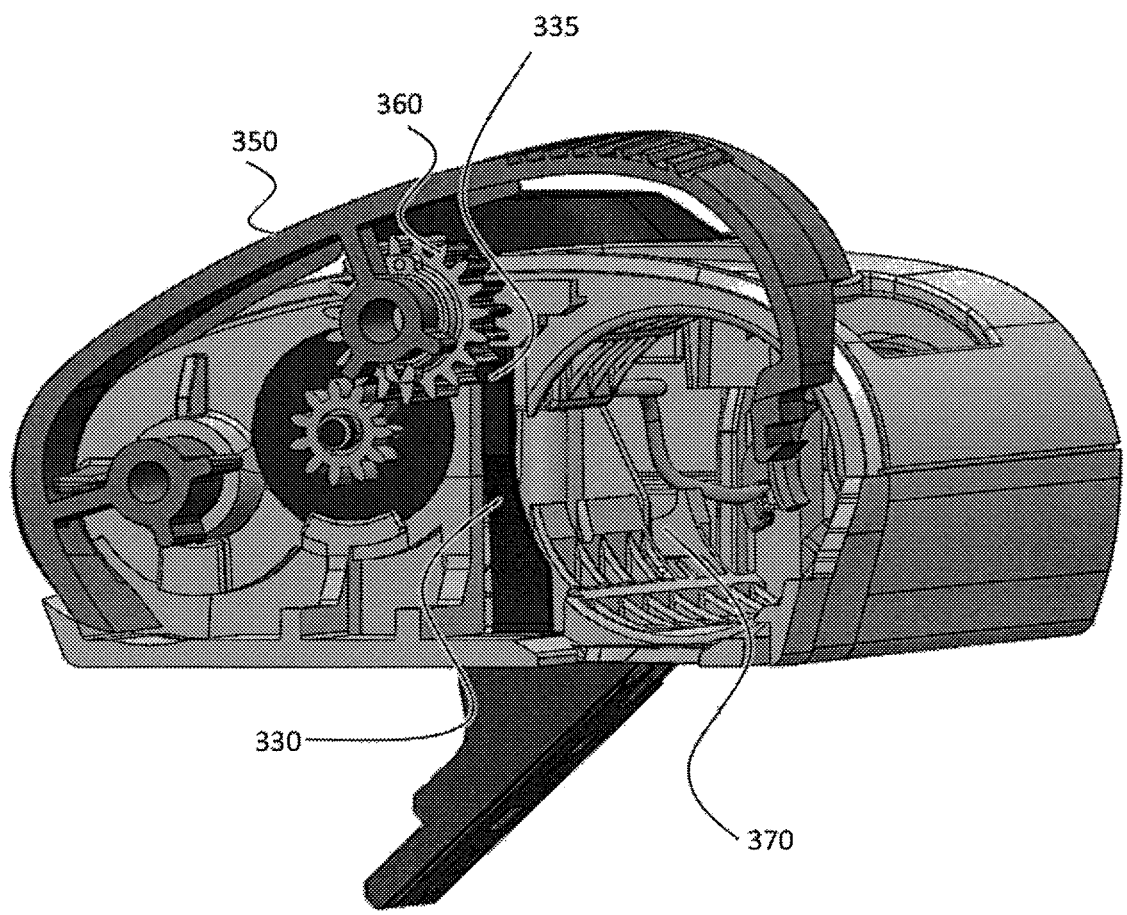

FIG. 6B Device with cartridge not fully inserted <95% the flexible arm still interfere with the gear preventing door closing
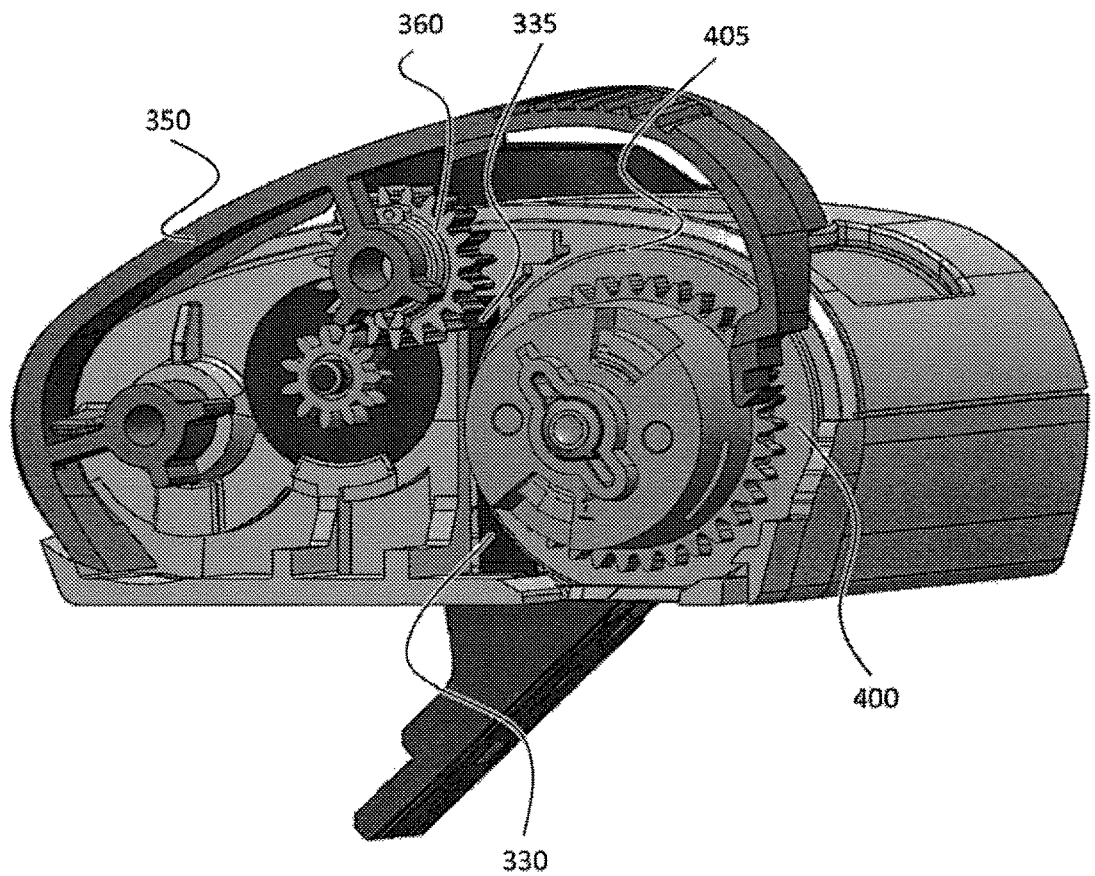

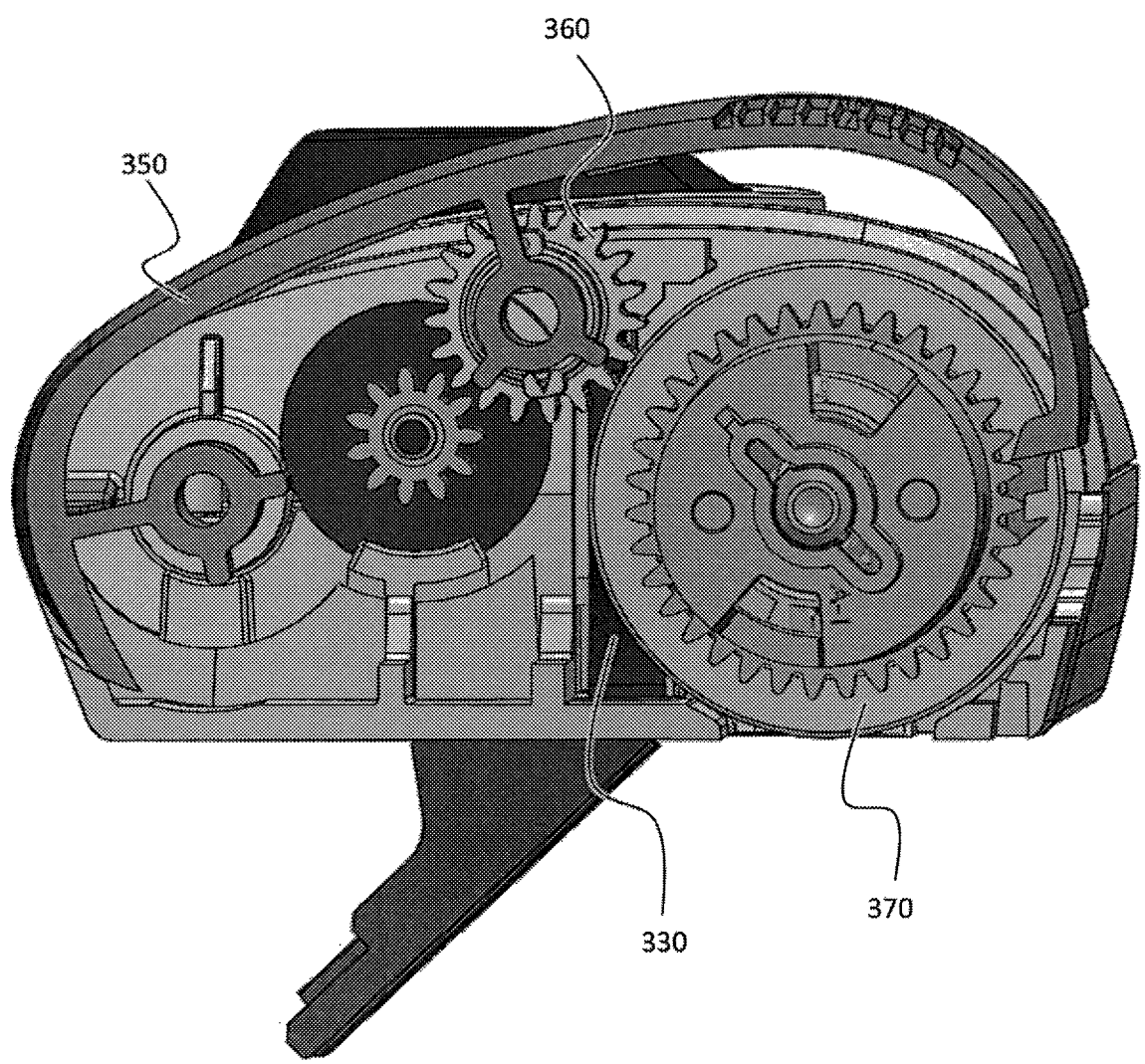
FIG. 6C Device with cartridge not fully inserted 95%. Cartridge flange interfere with gear and preventing the door from closing

FIG. 6D Device with cartridge fully inserted
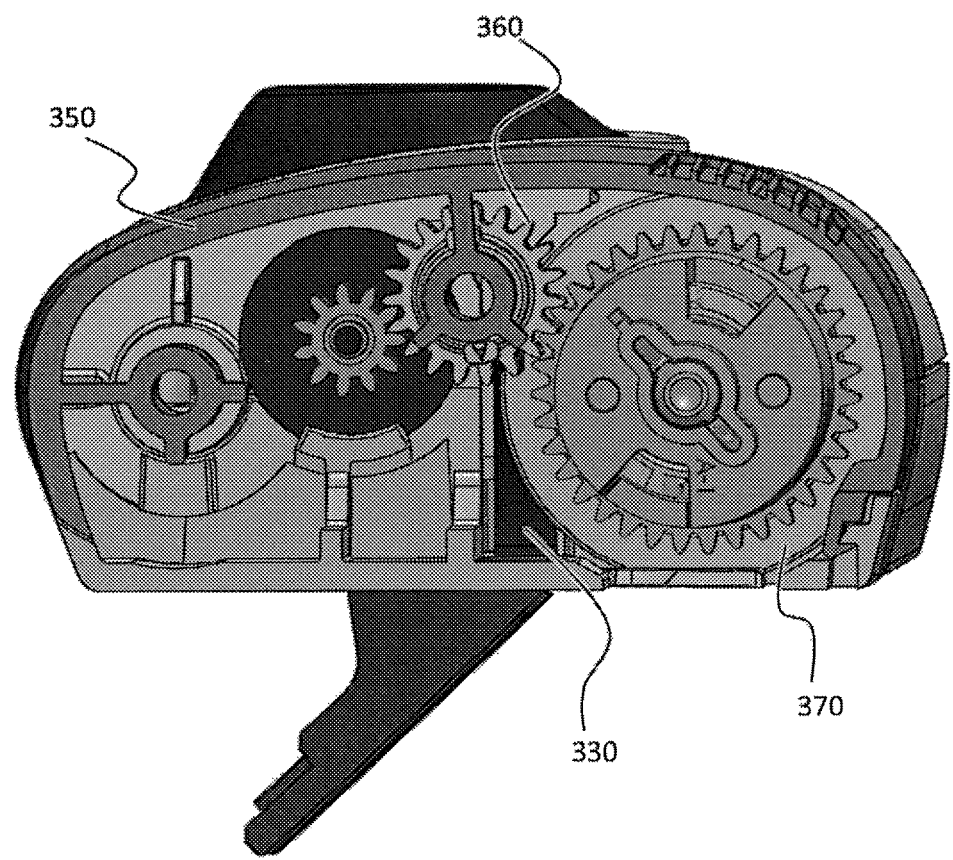

AUTOMATIC INJECTOR HAVING DOOR BLOCK UNTIL PROPER CARTRIDGE INSERTION

RELATED APPLICATIONS

This application claims the benefit of priority under 35 USC § 119(e) of U.S. Provisional Patent Application No. 62/369,513 filed on Aug. 1, 2016, the contents of which are incorporated herein by reference in their entirety.

FIELD AND BACKGROUND OF THE INVENTION

The present invention, in some embodiments thereof, relates to automatic injectors and, more particularly, but not exclusively, to a door block for proper insertion of a cartridge into an automatic injector.

U.S. Pat. No. 9,421,323 discloses a doorstop to a drug delivery apparatus that encourages a user of the apparatus to perform the proper usage steps in the proper order. For example, a user may be expected to receive an injector in a transport state, open it to an open state, insert a cartridge, and/or close the cartridge before operation. The doorstop may have an obstructing mode, optionally preventing closing of the door. The cartridge may optionally have a non-obstructing mode allowing closing of the door. Inserting the cartridge may optionally cause a doorstop to move from the obstructing mode to the non-obstructing mode. In the non-obstructing mode the doorstop may optionally prevent removal of the cartridge.

Additional background art includes U.S. Pat. Nos. 4,689,043, 5,090,877, 5,364,364, 5,445,621, 5,505,709, 5,779,676, 5,830,187, 5,954,697, 6,423,036, 6,599,272, U.S. Pat. Application Publication No. US2007/0197968, U.S. Patent Application Publication No. US2011/0066131, and International Application Publication No. WO2012032411A2.

SUMMARY OF THE INVENTION

Example 1. An automatic injector device for delivering a pharmaceutical substance from a cartridge having a protruding edge, the cartridge positioned in a housing of the device, the housing comprising a cartridge bay having an opening sized to allow passage of the cartridge into the cartridge bay; a door to the cartridge bay opening, the door connected to the housing and having an unlatched position and a latched position, the door defining a trajectory between the unlatched position and the latched position; an interference element having a deflected and an inflected orientation, the deflected orientation mechanically interferes with the trajectory of the door; and a contact interface positioned along the cartridge bay and extending up to the protruding edge, the contact interface mechanically couples the deflected and inflected orientation with a sensed contact of the protruding edge, such that when the protruding edge is positioned at the contact interface, the contact interface shifts the interference element into the inflected orientation.

Example 2. The device of example 1, wherein the door further comprises a coupling link, positioned to mechanically link the cartridge with a motor, when the door is in the latched position.

Example 3. The device of example 2, wherein the coupling link comprises a gear having cogs complementary to a powering gear of the motor and a driving gear of the cartridge.

Example 4. The device of example 3, wherein the driving gear is mechanically coupled to a plunger residing within the cartridge.

Example 5. The device of example 1, wherein the contact interface is positioned at a rim of the opening of the cartridge bay.

Example 6. The device of example 1, wherein the contact interface is elastic.

Example 7. The device of example 6, wherein the deflected orientation comprises an unstressed configuration of the interference element and the inflected orientation comprises a stressed configuration of the interference element.

Example 8. The device of example 6, wherein the contact interface mechanically interferes with a location of the protruding edge of the cartridge residing beyond the rim and outside of the cartridge bay.

Example 9. The device of example 8, wherein the location comprises a range of about 0.5 mm to about 3 mm beyond the rim and outside of the cartridge bay.

Example 10. The device of example 1, further comprising a cartridge lock positioned at the rim.

Example 11. The device of example 10, wherein the cartridge lock comprises a snap mechanism shaped to snap over a proximal edge of the cartridge and mechanically press against the cartridge, when the cartridge is positioned in the cartridge bay and the protruding edge contacts the contacts interface.

Example 12. The device of example 1, wherein a transition from the unlatched position to the latched position of the door is irrevocable.

Example 13. The device of example 12, wherein the door is pivotable about a first axis parallel to the cartridge bay and wherein the door is rotatable about a second axis which is perpendicular to the first axis.

Example 14. A method for amplifying a position of a cartridge having a protruding edge in a housing of an automatic injector, the housing having a door for closing the cartridge inserted into a cartridge bay of the housing, comprising mechanically interfering with a trajectory of closing the door through a deflected interference element; inserting the cartridge into the cartridge bay of the housing; pressing the protruding edge of the cartridge against a contact interface positioned along the cartridge bay, the contact interface mechanically coupled to the deflected interference element; shifting the position of the contact interface, thereby inflecting the interference element away from the trajectory of the door; and latching the door in a closed position.

Example 15. The method of example 14, wherein the latching the door in the closed position further comprises positioning a coupling link between a driving system of the cartridge and a motor of the injector.

Example 16. The method of example 14, wherein the inserting the cartridge further comprises inserting at least 95% of the cartridge before the protruding edge of the cartridge is pressed against the contact interface.

Example 17. The method of example 16, further comprising pushing the cartridge away from the cartridge bay when less than 95% of the cartridge is inserted.

Example 18. The method of example 17, wherein the pushing comprises preventing a proximal edge of the cartridge from residing in a range of about 0.5 mm to about 3 mm outside of the cartridge bay.

Example 19. The method of example 14, further comprising locking a position of the cartridge following the pressing of the protruding edge against the contact interface.

Example 20. The method of example 19, wherein the locking a position of the cartridge comprises locking the pressing of the protruding edge against the contact interface and locking the interference element in an inflected orientation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flow chart of inserting cartridge and closing the coupling link, in accordance with some embodiments of the invention;

FIG. 2 is a state diagram of cartridge insertion, in accordance with some embodiments of the invention;

FIGS. 3A-3B illustrate a perspective view of a schematic exemplary injector having an exemplary door block mechanism and being loaded with a cartridge, in accordance with some embodiments of the invention, wherein FIG. 3A illustrates an interfering position and FIG. 3B illustrates a non-interfering position;

FIGS. 3C-3D illustrate a perspective side view of a schematic exemplary door block mechanism and door trajectory, in accordance with some embodiments of the invention, wherein FIG. 3C illustrates an interfering position and FIG. 3D illustrates a non-interfering position;

FIGS. 3E-3F illustrate a side view of a schematic exemplary cartridge being inserted against a door block mechanism, in accordance with some embodiments of the invention, wherein FIG. 3E illustrates an interfering position and FIG. 3F illustrates a non-interfering position;

FIGS. 3G-3H illustrate a schematic example for a coupling link, in accordance with some embodiments of the invention, wherein FIG. 3G illustrates a coupling link positioned on an injector door and FIG. 3H illustrates the coupling link after the door is closed;

FIG. 4A is a perspective view of an unstressed interference element, in accordance with some embodiments of the invention;

FIG. 4B is an illustration of a door block mechanism, in accordance with some embodiments of the invention;

FIG. 5 is an exemplary system having a fully inserted cartridge, in accordance with some embodiments of the invention;

FIG. 6A is a rear view illustration of an example without an inserted cartridge, in accordance with some embodiments of the invention;

FIG. 6B is a rear view illustration of an example with a not-fully inserted cartridge wherein the interference element interferes with closing the door, in accordance with some embodiments of the invention;

FIG. 6C is a rear view illustration of an example with a not-fully inserted cartridge wherein the cartridge has pushed the interference element away from the trajectory of the door, but the cartridge itself is preventing closing the door, in accordance with some embodiments of the invention; and FIG. 6D is a rear view illustration of an example with a fully inserted cartridge resulting in an interference-free trajectory and a closed door, in accordance with some embodiments of the invention.

DESCRIPTION OF SPECIFIC EMBODIMENTS OF THE INVENTION

Figure 3A:
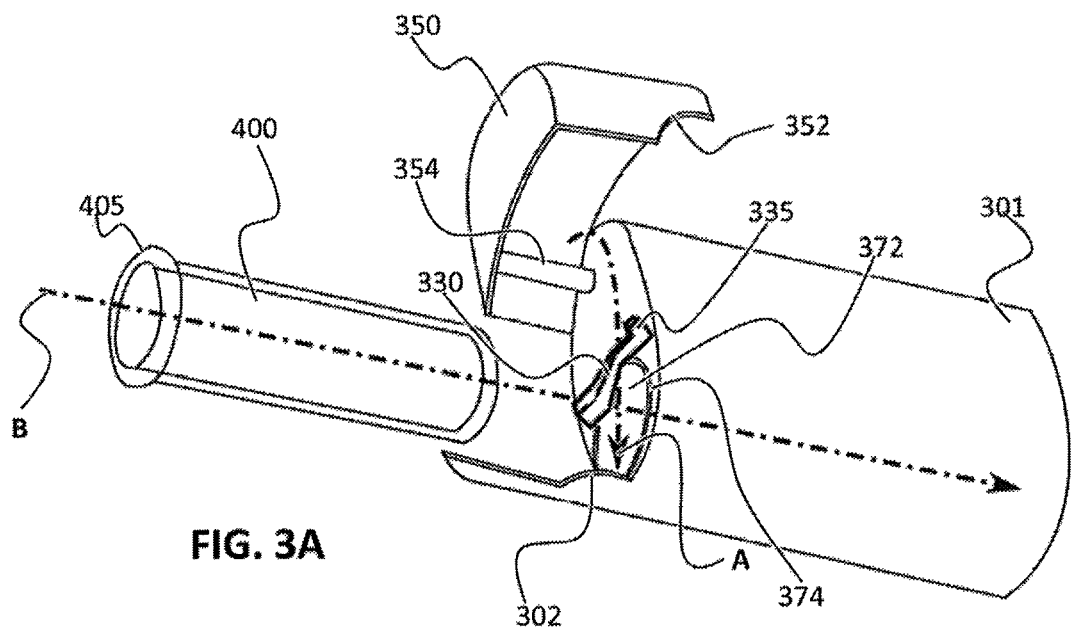

The present invention, in some embodiments thereof, relates to automatic injectors and, more particularly, but not exclusively, to a door block for proper insertion of a cartridge into an automatic injector.

Overview

An aspect of some embodiments of the invention relates to preventing an automatic injector door from locking into a closed position, as long as a cartridge is not inserted into the injector and/or as long as a cartridge is inserted but not properly positioned. In some embodiments, an improper position of the cartridge includes an improper mechanical interface, for example, an improper mechanical coupling of the cartridge to a motor and/or a gear of the injector. Alternatively or additionally, an improper position of the cartridge includes an improper fluid interface, for example, improper positioning of the cartridge with respect to the fluid path, for example, improper coupling of the cartridge with the needle, and/or improper positioning of a cartridge having a needle in the correct needle path of the injector. As used herein, a door comprises a cover which is fixed to the injector housing in one end, and allowed to transition between different states of covering the housing.

In some embodiments, an automatic injector comprises a door having a latching mechanism. Typically, an injector door is being closed once a cartridge is placed within the injector. A cartridge may be filled and/or pre-filled with a pharmaceutical substance, which may include for example, a drug, and/or placebo, and/or a nutritional supplement or the like. In some embodiments, a cartridge has a distal side being in fluid communication with a needle of the injector, and a proximal side having a plunger for driving the fluid through the fluid path. In order for the injector to work properly, a cartridge needs to have both a correct mechanical interface, permitting proper driving of the plunger, and a correct fluid interface permitting proper fluid communication from the cartridge to the needle and into an injection subject.

Optionally, the latching mechanism causes the door to close irrevocably, potentially identifying a used injector and preventing reuse of a disposable injector. In some embodiments, a cartridge which is not inserted properly into the injector interferes with a closing trajectory of the door and prevents its latching. Alternatively or additionally, an amplifier, which is affected by the cartridge position, mechanically interferes with closing the door when the cartridge is positioned improperly. It is a potential advantage to prevent a door from irrevocably closing without an inserted cartridge, for example, when preventing automatic injector devices from closing during transit. It is a potential advantage to prevent a door from irrevocably closing when the cartridge is not properly inserted, because operating the device while the cartridge is not in a proper position might result in fluid which would not be injected or be injected not through the fluid path, for example resulting in leakage. Alternatively or additionally, improper cartridge position may lead to gear malfunction and/or breakage.

An aspect of some embodiments of the invention relates to inhibiting operational communication to a cartridge of an automatic injector until the cartridge is sufficiently inserted into the injector device. In some embodiments, operational communication comprises engaging a driving mechanism with the cartridge, for example, by mechanically coupling a gear system to a plunger residing within the cartridge. In some embodiments, a mechanical coupling link is provided, optionally, being coupled to the injector door, for example, on an inner wall of the door.

In some embodiments, operational communication is determined by a state of a mechanical coupling link between the driving mechanism of the cartridge and a motor of the injector. For example, a coupling link may be a gear linking between a gear of the motor and a gear of the driving system of the plunger. Optionally, the state of the coupling link is characterized by at least two positions; an engaged position which enables mechanical operable communication between the cartridge and the motor, and a disengaged position in which the motor is disconnected from the driving mechanism of the cartridge. In some embodiments, an improper position of the cartridge prevents the coupling link to enter its engaged position.

In some embodiments, an injector comprises a cartridge bay sized and shaped for accommodating the cartridge, and having an opening for inserting the cartridge therethrough. Optionally, an injector door is hingedly connected to one side of the injector base, and is pivotally movable to its closing position resulting in covering the cartridge bay opening. In some embodiments, the door comprises a latching mechanism at the side of the door opposite to the hinge, and for locking with a complementary lock residing in the injector base opposite to the hinged connection with the door. In some embodiments, when the door is pivotally moved over the opening of the cartridge bay it defines a movement trajectory. Optionally, a coupling link residing in the door comprises a movement trajectory which follows the movement trajectory of the door. In some embodiments, a user gets a tactile feeling that the cartridge is misplaced by not being able to properly latch the door to the housing.

When the cartridge is improperly inserted into the injector, in some embodiments, the cartridge itself mechanically interferes with an engaged position of the coupling link. Optionally, a protruding edge of the cartridge interferes with a trajectory of positioning the coupling link. In some embodiments, a protruding edge includes a flange, and/or a bevel, and/or a knob, and/or a bulge. Optionally, the protruding edge extends along the entire perimeter of the cartridge, potentially enabling insertion of the cartridge without being sensitive to its rotational orientation.

Alternatively or additionally, when the cartridge is improperly positioned, an interference element mechanically interferes with transitioning the coupling link into its engaged position. Alternatively or additionally, an interference element mechanically interferes with the trajectory of closing the injector door. In some embodiments, the interference element is mechanically coupled to a sensor which detects the position of the cartridge. Optionally, the sensor couples an improper position of the cartridge with a presence of the interference element in the trajectory of the door and/or coupling link. Alternatively or additionally, the sensor couples a proper position of the cartridge with removing the interference element from the trajectory of the door and/or coupling link.

Optionally, the sensor is elastic. In some embodiments, when the cartridge is not fully inserted, the elastic sensor exerts a force on the cartridge, pushing it away from the cartridge bay, thereby enhancing the improper position of the cartridge. A potential advantage of enhancing the improper position of the cartridge is to prevent a user from operating an injector when the cartridge is positioned within the injector, but not in a proper manner. System failures sometimes occur when a device door is closed prematurely, without noticing the cartridge is not properly positioned. For example, in some cases a user may close the device door before inserting the cartridge fully into the injector. In other cases, the device door may close during transit. Some solutions prevent closing the door until the cartridge has been at least partially inserted, but do not prevent closing the door when the cartridge has been partially, but not fully, inserted.

Premature coupling of the driving mechanism with the plunger, may sometimes lead to system failure, potentially resulting in breakage of components of the injector and/or interfering with the injection of the injectable substance to a user of the injector.

In some embodiments, a sensor, for example a cartridge contact interface, detects the presence of the cartridge in a location proximal to the cartridge bay. In some embodiments, a sensor positioned at the rim of the opening of the cartridge bay provides mechanical feedback to the positioning of the cartridge with respect to the rim of the cartridge bay. In some embodiments, the sensor is elastic. In some embodiments, the sensor is positioned to be insensitive to the body of the cartridge, but to mechanically contact a distinct cross-section of the cartridge proximal end, for example a protruding edge.

In some embodiments, the sensor also prevent the cartridge from residing in a location being just outside the cartridge bay, forcing the cartridge to a location being even more remote than the opening, potentially amplifying the improper position by positioning the cartridge in a more noticeable configuration, visually and/or tactile wise. Optionally, the sensor interferes with positioning the protruding edge of the cartridge in a location being laterally to the rim and being outside of the cartridge bay, in the direction of the inserted cartridge. In case of incomplete cartridge insertion, the elastic sensor will pressure the cartridge outward extracting the cartridge from the bay and/or block the door from closing.

In some embodiments, a cartridge lock is provided to interlock the cartridge once it is inserted into the correct position. In some embodiments, an elastic door block combined with a cartridge lock (for example, locking the cartridge into position only when fully inserted) prevents door closure until the cartridge is fully inserted. In some embodiments, the configuration gives the user tactile feedback when the cartridge has been properly (fully) inserted, for example a click or a snap. Optionally, the configuration prevents removal of the cartridge after insertion.

An aspect of some embodiments of the invention relates to amplifying a position of a cartridge within an injector device. In some embodiments, a position of a cartridge indicates its success to correctly interface with the injector device. Optionally, interface with the injector includes a mechanical interface, such as for example, a plunger driving mechanism. Alternatively or additionally, interface with the injector includes a fluid interface, such as the fluid path from the cartridge, to the needle and eventually to an injection subject.

In some embodiments, amplifying includes mechanically coupling an interference element with the position of the cartridge, for example, by contacting a protruding cross-section of the cartridge with the interference element. Optionally, contacting is provided directly. Alternatively or additionally, contacting is provided indirectly, for example through a contact interface. In some embodiments, the interference element comprises a deflected orientation which interferes with a mechanical operation of the injector. For example, the deflected interference element may be positioned along a mechanical trajectory of closing a door of the injector. Alternatively or additionally, the interference element is positioned to prevent a coupling link for mechanically coupling a motor with a driving system of the fluid path.

A potential advantage of translating the cartridge position with an operational feature of the injector is that even a small malposition of the cartridge, which may be difficult to notice, is translated into an operational malfunction and/or tactile feedback which is easier to detect. In some embodiments, a malposition of the cartridge includes placing the proximal edge of the cartridge (i.e. the edge having the plunger and being opposite to the distal edge having the needle) in a location being no more than 0.5 mm, and/or no more than 1 mm, and/or no more than 2 mm, and/or no more than 3 mm, and/or no more than 4 mm, and/or no more than 5 mm from the opening of the cartridge bay, in a direction facing away from the cartridge bay.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Sequence of Events

Referring now to the drawings, FIG. 1 shows a flowchart of inserting a cartridge and closing an injector door, in accordance with some embodiments of the invention.

In some embodiments, an automatic injector is provided to a user without having the injectable matter, which is optionally supplied in a cartridge. In some embodiments, the cartridge is provided with a fluid outlet in its distal end and a plunger for driving the fluid out of the fluid outlet in its proximal end. In some embodiments, the automatic injector comprises a housing having a cartridge bay for accommodating the cartridge and a door for closing a proximal opening of the cartridge bay. Optionally, a door is coupled to a gear for coupling a powering gear of a motor to the driving gear of the plunger.

In some embodiments, an injector is supplied in 102 without a cartridge. In some embodiments, the door of the injector is blocked 104 from closing by an interference element. Optionally, an interference element interferes with a trajectory of closing the door as long as a cartridge is not inserted into the device. Potentially, preventing closing of the door without a cartridge eliminates irrevocable closing of the device by mistake, and/or during transit. It may also prevent operating the device without first inserting an injectable substance, such as found in the cartridge.

In some embodiments, a cartridge is inserted into the device in 106 but not sufficiently. In some embodiments, a cartridge which is not fully inserted into the device is a cartridge which comprises a proximal edge residing outside of the cartridge bay. For example, a cartridge has a body which has less than 99%, or less than 98%, or less than 97%, or less than 96%, or less than 95%, or less than 92%, or less than 90%, residing within the cartridge bay.

Alternatively or additionally, a cartridge is defined as not fully inserted when the cartridge is not properly coupled to an operational interface of the injector. In some embodiments, an operational interface is a fluid interface. Alternatively or additionally, an operational interface is a mechanical interface. In some embodiments, an injector properly operates by operably communication between a motor, a driving system, a plunger residing in a cartridge and a fluid outlet of the cartridge coupled to a needle. In some embodiments, a cartridge is provided after the operating components are supplied with the injector and it needs to be coupled correctly to the operational path. In some embodiments, an improper position of the cartridge with respect to the cartridge bay indicates an incorrect operable communication.

In some embodiments, when the cartridge is not fully inserted in 106, the door is still blocked for closing in 108. Optionally, the door is still blocked by the interference element blocking in 104. Alternatively or additionally, the door is blocked by the cartridge itself. In some embodiments, the cartridge comprises a protruding proximal edge, optionally interfering with closing the door. Optionally, the protruding edge of the cartridge extends along the entire circumference of the cartridge to reduce sensitivity to the insertion orientation of the cartridge. Alternatively, the protruding edge is provided in only a portion of the perimeter of the cartridge, potentially providing information regarding the orientation of the cartridge within the cartridge bay.

In some embodiments, a cartridge is fully inserted into the device in 112. In some embodiments, once the cartridge is fully inserted, feedback is provided to the interference element which causes it to inflect away from the trajectory of closing the door. Optionally, the cartridge is locked into place in 114, which, in some embodiments, results in the interference element being locked in its inflected orientation.

In some embodiments, once the cartridge is sufficiently inserted and the interference element is removed from the closing trajectory, the door is unblocked in 116 and can be closed 118. Optionally, the door is coupled 120 to a coupling link which serves as a mechanical connection between the mechanical interface of the injector, for example, connecting between a motor residing within the injector with a driving system of the plunger. In some embodiments, the supplied cartridge is preassembled with the driving system of the plunger and is optionally loaded into the injector with the driving system coupled to its proximal end.

Exemplary State of Events

Reference is now made to FIG. 2, showing a state diagram of cartridge insertion followed by closing the injector door, in accordance with some embodiments of the invention. Optionally the system can only go to the next state when the previous state is fully accomplished. Optionally, the system cannot return from one state to a previous state.

In some embodiments, an injector is supplied to a user without a cartridge. In some embodiments, the injector is provided with a deflected interference element 202. In some embodiments, the deflected interference element in 202 interferes with closing the device door leading to a blocked door 204. In some embodiments, as long as a cartridge is not inserted, the door remains blocked in 204. In some embodiments, as long as a cartridge is inserted but not fully inserted in 206, the interference element remains deflected in 208 and the door remains blocked in 210.

In some embodiments, once a cartridge is fully inserted in 212, it causes the interference element to be in an inflected state in 214. In some embodiments, once the cartridge is fully inserted in 212 it is also locked in place in 216. In some embodiments, the inflected interference element 214 no longer interferes with closing the door, leading to an unblocked door in 218. In some embodiments, an unblocked door 218 is closed 220, and optionally latched in the closed position, optionally irrevocably.

Exemplary Trajectories of Operation

Figure 3B:
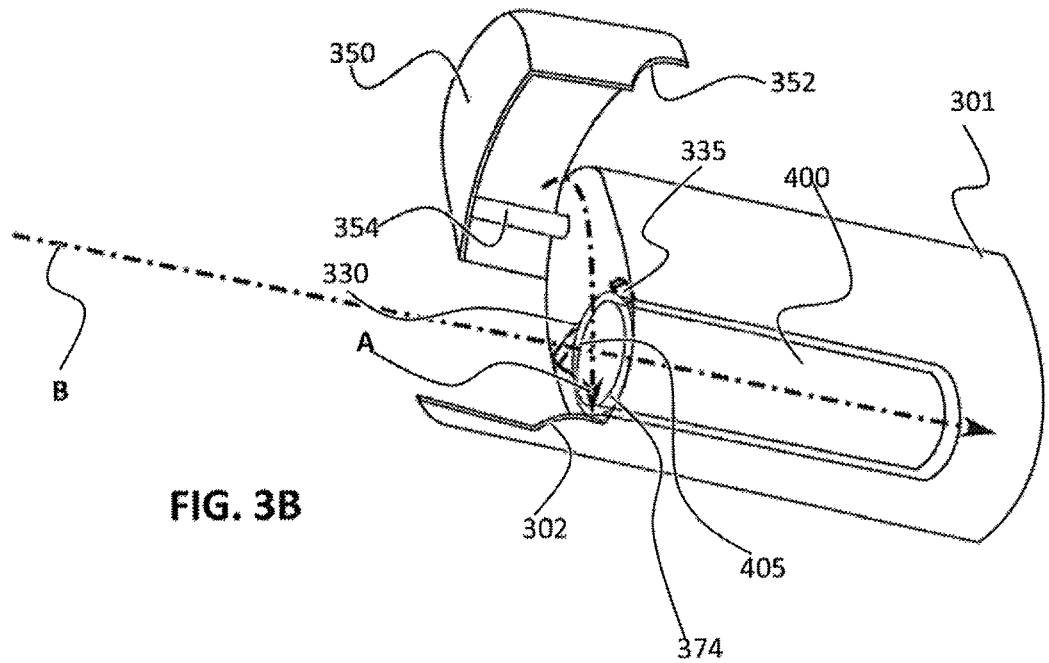

Reference is now made to FIGS. 3A-3B, illustrating schematic exemplary injector having an amplifier for a cartridge positioned improperly. An aspect of some embodiments of the invention relates to an elastic sensor for enhancing the detection of a position of a cartridge within an automatic injector.

In some embodiments, an injector is supplied with housing 301 having a cartridge bay 370 for accommodating cartridge 400. In some embodiments, housing 301 further comprises door 350 for closing the opening 372 of cartridge bay 370. In some embodiments, door 350 is hingedly connected to housing 301 through hinge 354. Optionally, door 350 closes over opening 372 by rotating about a first axis defined by hinge 354, and pivotally moving towards a second axis perpendicular to the first axis, resulting in door trajectory A.

In some embodiments, interference element 335 is positioned along the trajectory A, causing a mechanical interference for the movement of door 350 from an open position to a closed position. In some embodiments, an open position of door 350 is characterized by door 350 being unlatched to the housing, and a closed position of door 350 is characterized by door 350 being latched to the housing, optionally through latch 352 and complementary latch 302. For example, latch 352 may comprise a snap element, such as a pin, a dent, a bulge and the like, complementary to a dent, a pin or a bulge in complementary latch 302.

In some embodiments, interference element 335 is mechanically coupled to a cartridge contact interface 330. In some embodiments, contact interface 330 is positioned along the cartridge trajectory B of inserting cartridge 400, optionally along cartridge bay. In some embodiments, contact interface 330 intersects with a trajectory of a protruding element, for example, such as flange 405, comprised in cartridge 400. Optionally, the protruding element is provided in the proximal portion of cartridge 400. Alternatively or additionally, the protruding element is provided at the distal portion of cartridge 400, potentially indicative of the positioning of the fluid outlet of the cartridge.

In some embodiments, contact interface 330 extends into the trajectory B of cartridge 400 such that it interferes with the protruding element, but does not interfere with the body of the cartridge. Optionally, contact interface 330 is positioned at the rim 374 of opening 372. A potential advantage of placing the contact interface 330 at the rim 374 is its sensing of the cartridge position just outside the cartridge bay 370, which might be a position which due to its proximity to being fully within the cartridge bay, it may go unnoticed that the cartridge is not fully inserted. Alternatively or additionally, contact interface 330 is positioned inside the cartridge bay, optionally in proximity to the fluid path which is positioned at the distal end of the cartridge bay. In some embodiments, a mechanical connection, such as for example a rod, couples contact interface 330 with interference element 335.

In some embodiments, as long as the cartridge 400 is not inserted and/or not fully inserted into cartridge bay 370, interference element 335 is deflected into the trajectory A of door 350, as shown for example in FIG. 3A. In some embodiments, the deflected interference element 335 is in an unstressed state. Alternatively, the deflected orientation of the interference element 335 is its stressed state.

In some embodiments, once cartridge 400 is fully inserted into cartridge bay 370, protruding edge 405 presses against contact interface 330 and shifts its position. In some embodiments, once contact interface 330 shifts position it causes interference element 335 to inflect away from trajectory B, such as shown in FIG. 3B. Optionally, contact interface 330 is elastic. In some embodiments, protruding edge 405 presses against an unstressed contact interface 330, causing it to be pushed in the direction of trajectory B, i.e. towards the cartridge bay.

Optionally, once cartridge 400 is fully inserted, it is locked into place by cartridge locking mechanism 308, for example, a snap or a latch. In some embodiments, locking mechanism 308 presses cartridge 400 against contact interface 330 and retains its stressed position, optionally retaining the inflected orientation of the interference element 335.

Exemplary Door Blocking Mechanism

Reference is now made to FIGS. 3C-3F, illustrating a door blocking mechanism according to some embodiments of the invention. In some embodiments, door 350 connected at one side at hinge 354, is pivotally rotated along trajectory A into a closed position. The closing movement of door 350 is shown by the outline of moved door 350a.

In some embodiments, interference element 335 comprises a deflected orientation in which it interferes with trajectory A. Optionally, interference element 335 comprises protrusion 336, for example a pin, and/or a spike, and/or a rod, and/or a wand. In some embodiments, protrusion 336 further interferes with door 350, or with a feature residing in door 350, such as for example coupling link 360, exemplified in FIGS. 3G-3H.

In some embodiments, interference element 335 is mechanically coupled to contact interface 330. In some embodiments, contact interface comprises a surface extending into a trajectory B of inserting cartridge 400, as shown in FIG. 3E. In some embodiments, contact interface 330 is positioned at the rim 374 of opening 372 of cartridge bay 370, potentially sensing the position of cartridge 400 with respect to cartridge bay 370.

In some embodiments, as long as cartridge bay is not properly fitted with cartridge 400, contact interface 330 extends towards the direction of inserting cartridge 400, causing interference 335 to deflect into door trajectory A, as shown in FIG. 3C. In some embodiments, once a cartridge is properly fitted within cartridge bay 370, such as shown in FIG. 3F, contact interface 300 is pressed distally into the cartridge bay in the direction of insertion of cartridge 400, causing interference 335 to inflect away from trajectory A.

FIG. 3D shows an inflected orientation of interference 335 and the non-interfered door trajectory A, but the cartridge 400 is not shown in order to clearly see the mechanism.

Exemplary Gear Blocking Mechanism

Figure 3G:
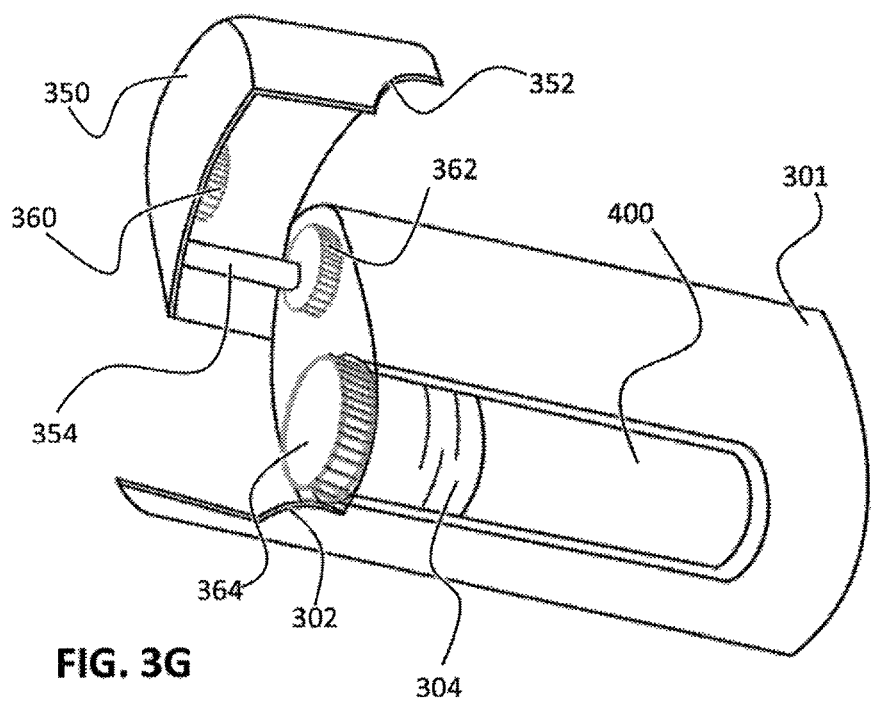
Figure 3H:
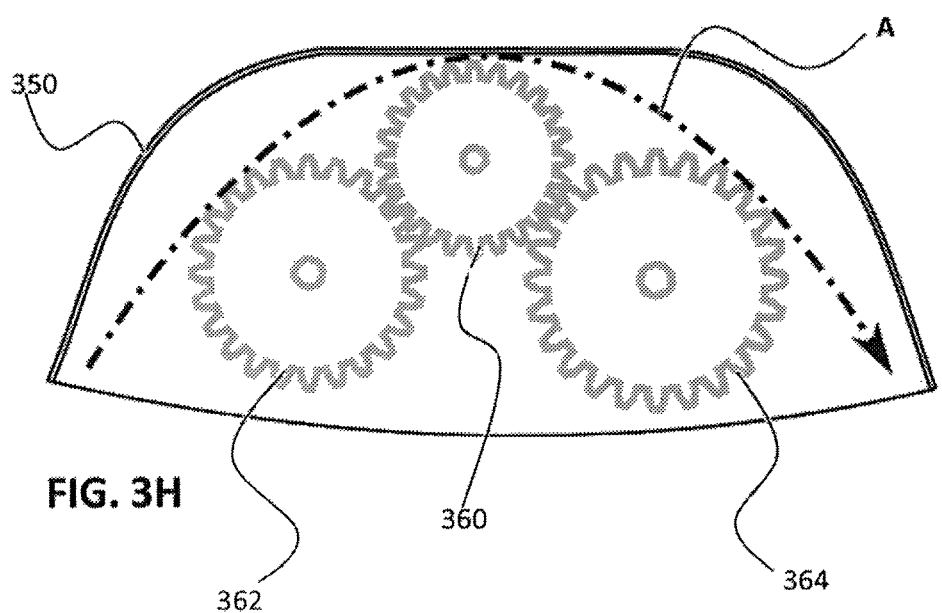

Reference is now made to FIGS. 3G-3H, showing blocking mechanism of an exemplary coupling link for a gearing system of an automatic injector, in accordance with some embodiments of the invention.

In some embodiments, door 350 is provided with coupling link 360. In some embodiments, coupling link 360 serves as a mechanical coupler between a motor of the injector, for example through powering gear 362, and the cartridge, for example through driving gear 364. In some embodiments, driving gear 364 is mechanically coupled to plunger 304. In some embodiments, operating driving gear 364 drives plunger 304 towards a fluid outlet of cartridge 400, driving fluid from within cartridge 400 and out into the fluid path of the automatic injector.

Optionally, coupling link 360 comprises a cogwheel. In some embodiments, the cogwheel comprises cogs which are complementary to the cogs in powering gear 362 and driving gear 364. In some embodiments, coupling link intefaces with powering gear 362 and driving gear 364 only when door 350 is closed. In some embodiments, interference element 335, and optionally protrusion 336, interferes directly with coupling link 360, preventing it to interface with powering gear 362 and driving gear 364 as long as cartridge 400 is not properly positioned.

Exemplary Door Blocking Elements

Reference is now made to FIG. 4A, illustrating a perspective view of an unstressed interference element before cartridge insertion, in accordance with some embodiments of the invention. The interference element protrudes into the path of the door and prevents closing the door.

In some embodiments, an automatic injector comprises a housing 301 having a cartridge bay 370 which comprises a cartridge contact interface 330. In some embodiments, contact interface 330 serves as a sensor for detecting the presence and/or position of a cartridge inserted into cartridge bay 370. In some embodiments, contact interface 330 is coupled to interference 335 serving in its deflected orientation as a mechanical block for door 350.

In some embodiments, contact interface 330 extends from a rim 374 of cartridge bay 370, optionally ventrally location, being opposite to the closing direction of door 350. A potential advantage of positioning contact interface 330 ventrally, is to save up on the width of the housing containing the contact interface 330 and its coupled interference element 335. However, it is possible that in some embodiments, contact interface is positioned at any other location along the perimeter of rim 374.

In some embodiments, a cartridge lock mechanism 308 is provided for locking in the cartridge once it is positioned correctly in cartridge bay 370. Optionally, cartridge lock 308 is positioned along rim 374.

Exemplary Door and Gear Blocking Elements

Reference is now made to FIG. 4B, illustrating a door and gear stop mechanism, in accordance with some embodiments of the invention. Shown here is a cartridge not fully inserted and the interference mechanism is in an unstressed state blocking the door.

In some embodiments, cartridge 400 is inserted into cartridge bay 370 by first inserting its distal end 404 having the fluid outlet, and lastly inserting its proximal end 402, optionally having flange 405. In some embodiments, once cartridge 400 is inserted sufficiently into cartridge bay 370, flange 405 presses against contact interface 330 and shifts it towards the distal end. In some embodiments, the coupled interference element 335 inflects away from the closing trajectory of door 350 and/or coupling gear 360, enabling to close the injector once the cartridge 400 is correctly placed.

Optionally, cartridge 400 is locked in this position even when the door is not closed, through lock 308.

Exemplary Closed Configuration

Reference is now made to FIG. 5, showing the cartridge fully inserted and the door closed, in a side cross-section of the automatic injector, and in accordance with some embodiments of the invention.

In some embodiments, as the cartridge 400 is fully pushed distally into the cartridge bay 370, the poximal flange 405 of the cartridge pushes a contact interface 330 of the door stopper in the distal direction, optionally flexing the door stopper and inflecting the interference element 335 out of the way of the door.

In some embodiments, once the cartridge 400 is fully inserted, a cartridge lock mechanism 308 locks the cartridge in place with the door stopper 335 out of the path of the door. Optionally, when the cartridge is locked, a user receives tactile feedback that the cartridge is in place. For example, the feedback may include a click of the lock mechanism and a cessation of proximal force pushing the cartridge out of the bay by the door stop interface, due to the proximal force exerted by the door stop being now held by the locking mechanism.

Exemplary Usage

Reference is now made to FIGS. 6A-6D, wherein FIG. 6A, is a rear view illustration of an embodiment without the cartridge 400 inserted, FIGS. 6B-6C are rear view illustrations of embodiments with the cartridge 400 not fully inserted, and FIG. 6D is a rear view illustration of an embodiment having the cartridge 400 fully inserted. In FIG. 6A, the interference element 335 blocks movement of a drive gear 360 connected to the door 350, preventing closure of the door 350.

When a cartridge is inserted, but not sufficiently, as shown in FIGS. 6B and 6C, the door 350 cannot close due to mechanical interference. In some embodiments, such as shown in FIG. 6B, when the cartridge is inserted to the extent that it does not mechanically engage with contact interface 330, then interference element 335 is not deflected away from the trajectory of door 350 and the door is inhibited from closing. In some embodiments, when the cartridge is inserted to the extent that it does engage with contact interface 330 and therefore causing the interference element 335 to deflect, if the cartridge is still not fully inserted then the cartridge flange 405 mechanically interferes with the trajectory of closing the door.

In some embodiments, contact interface 330 is elastic, and when the cartridge is not fully inserted, contact interface 330 exerts an opposing force to the insertion of the cartridge, causing the cartridge to stick out of the cartridge bay 370, amplifying the presence of the cartridge in an improper position.

Once the cartridge is inserted at FIG. 6D, the locking mechanism 308 blocks rearward (proximal) movement of the rear (proximal) flange 405 of the cartridge 400, locking the cartridge in the fully inserted position. The proximal flange 405 of the cartridge 400 pushes the contact interface 330 forward (distally) so that the drive gear 360 clears the interference element 335 allowing the door to close.

General

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An automatic injector device for delivering a pharmaceutical substance from a cartridge having a protruding edge, said cartridge positioned in a housing of said device, said housing comprising:
    a cartridge bay having an opening sized to allow passage of said cartridge into said cartridge bay;
    a door to said cartridge bay opening, said door having an unlatched position and a latched position, said door being configured to move between the unlatched position and the latched position along a trajectory;
    an interference element having a deflected orientation comprising an unstressed configuration of said interference element and an inflected orientation comprising a stressed configuration of said interference element, wherein said interference element is configured to mechanically interfere with movement of said door along said trajectory in said deflected orientation, and wherein said interference element is configured to not mechanically interfere with movement of said door along said trajectory in said inflected orientation; and
    a contact interface that is elastic and positioned along said cartridge bay such that when said protruding edge engages said contact interface, said contact interface shifts said interference element into said inflected orientation.

2. The device of claim 1, wherein said door further comprises a coupling link positioned to mechanically link said cartridge with a motor when said door is in the latched position.

3. The device of claim 2, wherein said coupling link comprises a gear having cogs complementary to a powering gear of said motor and a driving gear of said cartridge.

4. The device of claim 3, wherein said driving gear is mechanically coupled to a plunger disposed within said cartridge.

5. The device of claim 1, wherein said contact interface is positioned at a rim of said opening of said cartridge bay.

6. The device of claim 5, wherein said contact interface mechanically interferes with a location of said protruding edge of said cartridge residing beyond said rim and outside of said cartridge bay.

7. The device of claim 6, wherein said location comprises a range of about 0.5 mm to about 3 mm beyond said rim and outside of said cartridge bay.

8. The device of claim 6, further comprising a cartridge lock positioned at said rim.

9. The device of claim 8, wherein said cartridge lock comprises a snap mechanism shaped to snap over a proximal edge of said cartridge and mechanically press against said cartridge when said cartridge is positioned in said cartridge bay and said protruding edge contacts said contacts interface.

10. The device of claim 1, wherein a transition from said unlatched position to said latched position of said door is irrevocable.

11. The device of claim 10, wherein said door is pivotable about a first axis parallel to said cartridge bay and wherein said door is rotatable about a second axis which is perpendicular to the first axis.

12. A method for positioning a cartridge having a protruding edge in a housing of an automatic injector, said housing having a door for covering a cartridge bay of said housing that is configured to receive the cartridge, the method comprising:
- mechanically interfering, via a deflected interference element that is in an unstressed configuration, with movement of said door through a trajectory of closing said door;
- inserting said cartridge into said cartridge bay of said housing;
- pressing said protruding edge of said cartridge against a contact interface that is elastic and positioned along said cartridge bay;
- shifting the position of said contact interface, thereby inflecting said interference element into a stressed configuration away from said trajectory of said door; and
- latching said door in a closed position.

13. The method of claim 12, wherein latching said door in said closed position further comprises positioning a coupling link between a driving system of said cartridge and a motor of said injector.

14. The method of claim 12, wherein inserting said cartridge further comprises inserting at least 95% of said cartridge before said protruding edge of said cartridge is pressed against said contact interface.

15. The method of claim 12, further comprising locking a position of said cartridge following pressing of said protruding edge against said contact interface.

16. The method of claim 15, wherein locking a position of said cartridge comprises locking said protruding edge against said contact interface and locking said interference element in an inflected orientation.

17. A method for positioning a cartridge having a protruding edge in a housing of an automatic injector, said housing having a door for covering a cartridge bay of said housing that is configured to receive the cartridge, the method comprising:
- mechanically interfering, via a deflected interference element, with movement of said door through a trajectory of closing said door;
- pushing said cartridge away from said cartridge bay when less than 95% of said cartridge is inserted into said cartridge bay;
- inserting at least 95% of said cartridge into said cartridge bay of said housing before said protruding edge of said cartridge is pressed against a contact interface;
- pressing said protruding edge of said cartridge against said contact interface positioned along said cartridge bay;
- shifting the position of said contact interface, thereby inflecting said interference element away from said trajectory of said door; and
- latching said door in a closed position.

18. The method of claim 17, wherein pushing said cartridge comprises preventing a proximal edge of said cartridge from residing in a range of about 0.5 mm to about 3 mm outside of said cartridge bay.

* * * * *